United States Patent
Samadani et al.

(10) Patent No.: US 11,839,482 B2
(45) Date of Patent: Dec. 12, 2023

(54) MONITORING SWALLOWING IN A SUBJECT

(71) Applicant: KONINKLIJKE PHILIPS N.V., Eindhoven (NL)

(72) Inventors: Ali Akbar Ahmad Samadani, Somerville, MA (US); Leslie Altimier, Newburyport, MA (US); Louis Nicolas Atallah, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 416 days.

(21) Appl. No.: 17/254,882

(22) PCT Filed: Jun. 24, 2019

(86) PCT No.: PCT/EP2019/066579
§ 371 (c)(1),
(2) Date: Dec. 22, 2020

(87) PCT Pub. No.: WO2020/002181
PCT Pub. Date: Jan. 2, 2020

(65) Prior Publication Data
US 2021/0259623 A1    Aug. 26, 2021

Related U.S. Application Data (60) Provisional application No. 62/690,111, filed on Jun. 26, 2018.

(30) Foreign Application Priority Data

Jul. 24, 2018   (EP) .................................... 18185174

(51) Int. Cl.
*A61B 5/00*   (2006.01)
*G16H 40/67*  (2018.01)
*G06N 3/044*  (2023.01)

(52) U.S. Cl.
CPC ............ *A61B 5/4205* (2013.01); *A61B 5/687* (2013.01); *A61B 5/6847* (2013.01);
(Continued)

(58) Field of Classification Search
CPC ...... A61J 15/008; A61J 15/0003; A61J 15/00; A61B 5/4205
See application file for complete search history.

(56) References Cited

U.S. PATENT DOCUMENTS

2006/0152309 A1*  7/2006  Mintchev ............... H02N 15/00
                                          335/58
2010/0145166 A1*  6/2010  Pickler .................... A61B 5/163
                                          600/301
(Continued)

FOREIGN PATENT DOCUMENTS

EP    3190421 A1   7/2017
WO    2013086615 A1   6/2013
(Continued)

OTHER PUBLICATIONS

International Search Report and Written Opinion, International Application No. PCT/EP2019/066579, dated Sep. 18, 2019.
(Continued)

*Primary Examiner* — Eric F Winakur
*Assistant Examiner* — Elina Sohyun Ahn (57) ABSTRACT

There is provided an apparatus (100) for monitoring swallowing in a subject. The apparatus (100) comprises a processor (102) configured to acquire, from a motion sensor (104), motion signals obtained from a feeding tube, when placed in the esophagus of the subject. The motion signals are indicative of swallowing motions transmitted along the feeding tube. The processor (102) is also configured to
(Continued)

process the acquired motion signals to classify the acquired motion signals as indicative of the subject swallowing healthily or unhealthily.

11 Claims, 4 Drawing Sheets

(52) U.S. Cl.
CPC ........... *A61B 5/7264* (2013.01); *G06N 3/044* (2023.01); *G16H 40/67* (2018.01); *A61B 2562/0219* (2013.01)

(56) References Cited

U.S. PATENT DOCUMENTS

| | | |
|---|---|---|
| 2014/0228714 A1 | 8/2014 | Chau et al. |
| 2014/0343415 A1 | 11/2014 | Hoffman et al. |
| 2018/0078195 A1* | 3/2018 | Sutaria ..................... A61B 7/00 |
| 2019/0038208 A1* | 2/2019 | Mohammadi ........ A61B 5/4205 |
| 2020/0129380 A1* | 4/2020 | Sazonov .............. A61B 5/4205 |

FOREIGN PATENT DOCUMENTS

| | | |
|---|---|---|
| WO | 2014081401 A1 | 5/2014 |
| WO | 2015154960 A1 | 10/2015 |
| WO | 2016187456 A1 | 11/2016 |
| WO | 2017200885 A1 | 11/2017 |

OTHER PUBLICATIONS

O'horo JC, Rogus-Pulia N, Garcia-Arguello L, Robbins J, Safdar N. Bedside diagnosis of dysphagia: a systematic review. Journal of hospital medicine. Apr. 1, 2015;10(4):256-65.

Lagarde ML, Kamalski DM, Van Den Engel-Hoek L. The reliability and validity of cervical auscultation in the diagnosis of dysphagia: a systematic review. Clinical rehabilitation. Feb. 2016;30(2):199-207.

Lee J, Steele CM, Chau T. Time and time-frequency characterization of dual-axis swallowing accelerometry signals. Physiological measurement. Aug. 28, 2008;29(9):1105-1120.

Stroud AE, Lawrie BW, Wiles CM. Inter and intra-rater reliability of cervical auscultation to detect aspiration in patients with dysphagia. Clinical rehabilitation. Sep. 2002; 16(6):640-5.

* cited by examiner

MONITORING SWALLOWING IN A SUBJECT

This application is the U.S. National Phase application under 35 U.S.C. § 371 of International Application No. PCT/EP2019/066579, filed on 24 Jun. 2019, which claims the benefit of U.S. Provisional Application No. 62/690,111, filed on 26 Jun. 2018 and European Application Serial No. 18185174.2, filed 24 Jul. 2018. These applications are hereby incorporated by reference herein.

FIELD OF THE INVENTION

The disclosure relates to an apparatus and method of operating the apparatus for monitoring swallowing in a subject.

BACKGROUND OF THE INVENTION

In certain situations, particularly in a hospital setting, it can be important to monitor swallowing in a subject. For example, swallowing and oral feeding health is one of the key factors that is considered for discharging a subject from an intensive care unit or a medical facility (e.g. hospital). It is useful to enable continuous monitoring of swallowing health to aid clinicians in deciding the timing and progression of independent oral feeding of the subject and, eventually, discharge of the subject. The failure to timely assess when a subject is capable of swallowing without difficulties is among the top causes for longer stays in intensive care units or medical facilities (e.g. hospitals).

The medical term used for swallowing difficulties is dysphagia and this may include the impaired pharyngeal phase of swallowing. The impaired pharyngeal phase of swallowing is common in subjects with neurological disorders and can also be common in premature infants. The impaired swallowing in a subject can result in complications, such as prandial aspiration (which is the entry of food into the airway) and/or pharyngeal residue, which in turn can pose serious health risks such as aspiration, malnutrition, dehydration, and even death. A difficulty that arises in detecting impaired swallowing in a subject is that the impaired swallowing can be silent (e.g. without any overt signs of swallowing difficulty such as coughing). This means that swallowing impairment is difficult to detect via clinical perceptual judgment.

As such, the most popular technique that is currently used for tracking swallowing activities is videofluoroscopy, which enables clinicians to monitor barium-infused feedings during swallowing via moving x-ray images. However, a videofluoroscopy swallowing study (VFSS) cannot be performed on a routine basis due to it requiring sophisticated and expensive equipment, excessive amounts of harmful radiation, expensive procedures, as well as the need for specialized medical personnel. Another technique to assess swallowing activities in a subject is the flexible endoscopic evaluation of swallowing with sensory testing (FEESST). However, this technique also requires specially-trained medical personnel for set-up and operation. Moreover, each of the existing techniques described earlier are invasive.

There are a number of non-invasive alternatives for monitoring swallowing in a subject, which include surface electromyography, pulse oximetry, cervical auscultation (which involves listening to the breath sounds near the larynx), and swallowing accelerometry. However, despite the introduction of different non-invasive approaches, the reliable and accurate non-invasive detection of swallowing abnormalities or difficulties in a subject remains a challenging task. For example, a recent systematic review of cervical auscultation studies suggests that the reliability of this approach is insufficient and cannot be used as a stand-alone instrument to diagnose dysphagia.

Another shortcoming associated with existing non-invasive techniques is that they do not explicitly address swallowing difficulties in premature infants. Premature infants lack the maturational and developmental ability to coordinate suck-swallow-respiration cycles. Fetal ultrasound demonstrates that sucking and swallowing first occur as relatively separate actions and, over time, become inter-related. Early coordination of suck-swallow begins at about 32-34 weeks. With maturation, around 34-37 weeks post menstrual age (PMA), the infant becomes more rhythmical, fluid, and efficient in alternating suck positive pressure and negative pressure. Until this occurs, premature infants demonstrate swallowing difficulties, which are among the most common disorders in premature infants. A self-coordinated and matured oral feeding is thus a key factor in preparing premature infants for neonatal intensive care unit (NICU) discharge. It is especially important that any technique used to monitor swallowing in premature infants is non-invasive due to their vulnerability. However, the non-invasive techniques that are currently available are not suitable for premature infants.

For example, US 2014/0228714 discloses a technique for swallowing impairment detection. In this technique, a dual-axis accelerometer is positioned on the neck of the subject (e.g. by way of a strap, elasticized band and/or double-sided adhesive tape) to track swallowing events in the subject. However, while this technique is non-invasive, it can cause the subject discomfort and can even be damaging to the skin of subject, particularly in the case of vulnerable subjects such as premature infants. Moreover, this technique relies on epidermal cervical accelerations that can be obscured by skin sagginess, subcutaneous fat in the neck area and, generally, the limited neck area in the case of premature infants. Moreover, due to swallowing being detected from outside the body of the subject in such non-invasive techniques, the results of this detection can be unreliable compared to invasive techniques that monitor swallowing from inside the body of the subject. For example, the detection of swallowing from outside the body of the subject using microphones is more susceptible to contamination from other sounds and variable sources, which can make it difficult to isolate activities that are specific to swallowing.

SUMMARY OF THE INVENTION

As noted above, a limitation with existing techniques is that it is not possible to non-invasively monitor swallowing in a reliable manner and without causing discomfort to the subject beyond that which the subject is already experiencing. It would thus be valuable to have an improvement to address the existing problems.

Therefore, according to a first aspect, there is provided an apparatus for monitoring swallowing in a subject. The apparatus comprises a processor. The processor is configured to acquire, from a motion sensor, motion signals obtained from a feeding tube, when placed in the esophagus of the subject. The motion signals are indicative of swallowing motions transmitted along the feeding tube. The processor is also configured to process the acquired motion signals to classify the acquired motion signals as indicative of the subject swallowing healthily or unhealthily.

In some embodiments, the motion signals may be obtained from a portion of the feeding tube positioned outside the body of the subject. In some embodiments, the motion sensor may be positioned remote from the body of the subject.

In some embodiments, the motion sensor may comprise an accelerometer positioned on the feeding tube. In some embodiments, the accelerometer may comprise any one or more of a bi-axial accelerometer and a tri-axial accelerometer. In some embodiments, the accelerometer may comprise a tri-axial accelerometer and the acquired motion signals may comprise motion signals acquired in a superior-inferior direction, an anterior-posterior direction, and a lateral-medial direction. In some embodiments, the motion sensor may comprise a visual sensor directed at the feeding tube.

In some embodiments, the feeding tube, when placed in the esophagus of the subject, may be positioned in a vicinity of an epiglottis and/or a hyoid bone of the subject.

In some embodiments, the processor may be configured to extract one or more features indicative of swallowing activities from the acquired motion signals and decompose the acquired motion signals into a plurality of different segments based on the one or more extracted features. In some of these embodiments, the processor may be configured to process the acquired motion signals by being configured to process the plurality of different segments to classify the acquired motion signals as indicative of the subject swallowing healthily or unhealthily.

In some embodiments, the processor may be configured to process the acquired motion signals using a gated recurrent deep neural network to classify the acquired motion signals as indicative of the subject swallowing healthily or unhealthily.

In some embodiments, the processor may be configured to process the acquired motion signals by being configured to process the acquired motion signals to classify the acquired motion signals as indicative of the subject swallowing healthily or unhealthily according to one or more predefined reference features that are indicative of the subject swallowing healthily or unhealthily.

In some embodiments, the processor may be further configured to determine whether the subject is ready for independent oral feeding based on whether the acquired motion signals are classified as indicative of the subject swallowing healthily or unhealthily.

According to a second aspect, there is provided a system comprising the apparatus described earlier and the motion sensor mentioned earlier. The motion sensor is configured to obtain the motion signals from the feeding tube, when placed in the esophagus of the subject.

According to a third aspect, there is provided a method of operating an apparatus for monitoring swallowing in a subject. The method comprises acquiring, by a processor from a motion sensor, motion signals obtained from a feeding tube, when placed in the esophagus of the subject. The motion signals are indicative of swallowing motions transmitted along the feeding tube. The method also comprises processing, by the processor, the acquired motion signals to classify the acquired motion signals as indicative of the subject swallowing healthily or unhealthily.

According to a fourth aspect, there is provided a computer program product comprising a computer readable medium, the computer readable medium having a computer readable code embodied therein, the computer readable code being configured such that, on execution by a suitable computer or processor, the computer or processor is caused to perform the method described above.

According to the aspects and embodiments described above, the limitations of existing techniques are addressed. In particular, according to the above-described aspects and embodiments, it is possible to non-invasively monitor swallowing in a more reliable and more accurate manner without causing discomfort to the subject beyond that which the subject is already experiencing. Due to the prevalence of swallowing disorders, feeding tubes are commonly used for feeding a subject. The above-described aspects and embodiments appreciate that a feeding tube is often, if not always, present in a subject that is experiencing swallowing difficulties and thus makes use of the already present feeding tube to monitor swallowing in the subject. As such, it is not necessary for additional sensors or devices to be applied to the body of the subject or inserted into the subject. Instead, the above-described aspects and embodiments can be used to monitor motion (e.g. vibrations) transmitted by the feeding tube that is already present inside the esophagus of the subject. The technique according to above-described aspects and embodiments is not only non-invasive but also requires minimal modification to existing feeding tubes.

Moreover, since the actual motion transmitted along the feeding tube as a result of the subject swallowing can be tracked from inside the esophagus of the subject, it is possible to achieve more reliable and more accurate monitoring of swallowing in the subject. For example, the technique according to the above-described aspects and embodiments is less susceptible to contamination from other sounds and variable sources. The technique according to the above-described aspects and embodiments also enables efficient and user-friendly monitoring, which can aid clinicians in the implementation of timely feeding or swallowing interventions for the subject and can also provide clinicians with an improved indication as to whether a subject can be discharged. In this way, it is possible to decrease a length of stay of a subject in an intensive care unit or medical facility (e.g. a hospital).

There is thus provided an improved apparatus, system, method, and computer program product for monitoring swallowing in a subject, which is aimed at overcoming existing problems.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

As noted above, there is provided herein an improved apparatus, system, method, and computer program product for monitoring swallowing in a subject, which is aimed at overcoming existing problems. The subject that is referred to herein may be an adult or a pediatric subject, e.g. an infant, a child or an adolescent. An infant can, for example, be a neonate, such as a pre-term or premature infant, a full-term infant or a post-term infant. In some embodiments, the subject that is referred to herein may be a patient or any other subject. The subject can be any subject that relies on a feeding tube, e.g. due to a swallowing impairment (such as dysphagia and/or other swallowing impairments).

Figure 1:
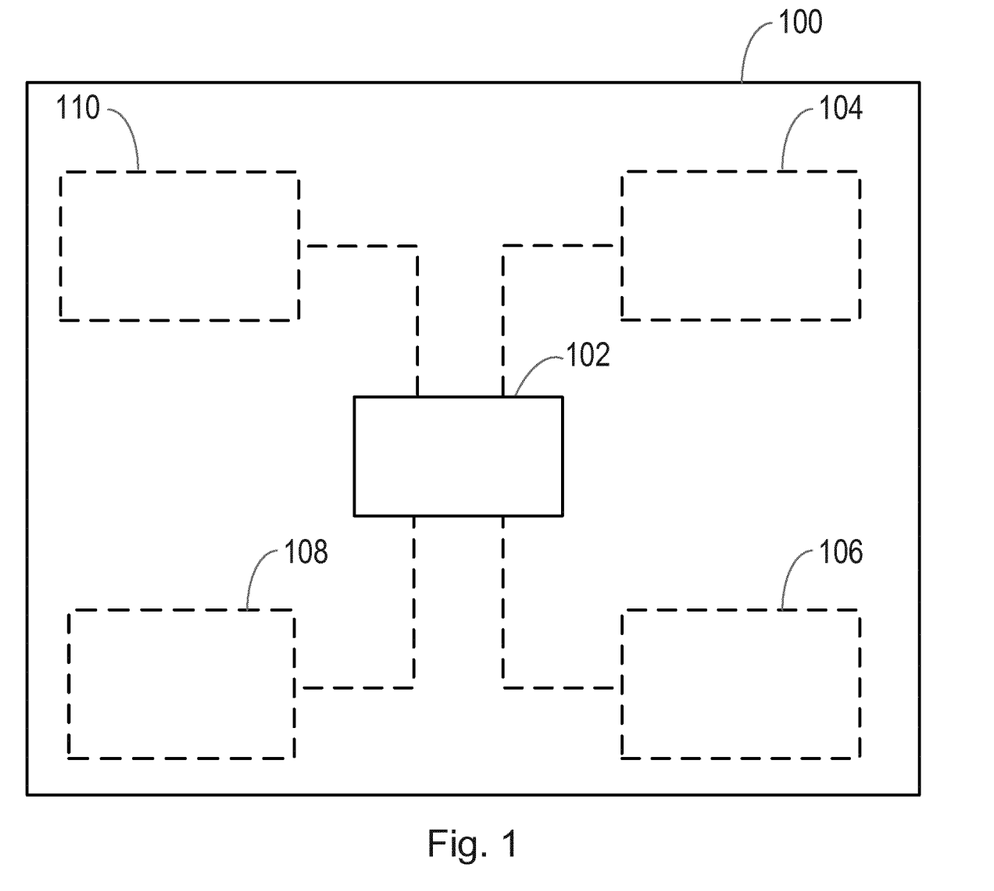
FIG. 1 is a block diagram of an apparatus according to an embodiment.

FIG. 1 illustrates an apparatus 100 for monitoring swallowing in a subject according to an embodiment. As illustrated in FIG. 1, the apparatus 100 comprises a processor 102. Briefly, the processor 102 of the apparatus 100 is configured to acquire, from a motion sensor 104, motion signals obtained from a feeding tube, when the feeding tube is placed (or located) in the esophagus of the subject. The motion signals are indicative of swallowing motions transmitted along the feeding tube. For example, the motion signals can be indicative of lateral and/or longitudinal swallowing motions transmitted along the feeding tube.

In more detail, when the subject swallows, the action of swallowing generates movement along the esophagus of the subject and this generated movement can vibrate the feeding tube. These vibrations that are caused by swallowing motions transmitted along the feeding tube can thus be captured as motion signals. In some embodiments, the acquired motion signals can comprise sequences of a time-series of motion signals.

Returning to FIG. 1, the processor 102 of the apparatus 100 is configured to process the acquired motion signals to classify the acquired motion signals as indicative of the subject swallowing healthily or unhealthily. For example, in some embodiments, the processor 102 of the apparatus 100 may be configured to classify the acquired motion signals as indicative of the subject swallowing healthily or unhealthily by being configured to map the acquired motion signals to healthy versus unhealthy swallows. In some embodiments, for example, the processor 102 of the apparatus 100 can be configured to compare the acquired motion signals with predefined classification criteria (e.g. a previously classified training data set) representative of healthy and unhealthy swallows to classify the acquired motion signals as indicative of the subject swallowing healthily or unhealthily. For example, the processor 102 may be configured to extract, from the acquired motion signals, one or more preset features representative of a swallowing event and compare the one or more extracted features with the predefined classification criteria (which may be defined as a function of the preset features) to classify the acquired motion signals as indicative of the subject swallowing healthily or unhealthily. In some embodiments, the classification criteria may be defined (e.g. set or established) by a medical professional, such as based on medical data, medical requirements and/or medical trials.

In some embodiments, the processor 102 of the apparatus 100 may be configured to classify the acquired motion signals as indicative of the subject swallowing unhealthily where the acquired motion signals are indicative of any one or more of pharyngeal residue, aspiration, and penetration. Thus, the processor 102 of the apparatus 100 described herein is configured to classify the acquired motion signals into one of two categories, namely into the category of healthy swallowing or the category of unhealthy swallowing. In some embodiments, these categories may comprise a plurality of sub-categories. For example, as mentioned earlier, the category of unhealthy swallowing may comprise the sub-categories of pharyngeal residue, aspiration, and penetration.

In some embodiments, the processor 102 of the apparatus 100 may be configured to classify the acquired motion signals as indicative of the subject swallowing healthily where the processor 102 detects that the acquired motion signals comprises no features that are indicative of the subject experiencing swallowing difficulties (e.g. a swallowing impairment). Similarly, the processor 102 of the apparatus 100 may be configured to classify the acquired motion signals as indicative of the subject swallowing unhealthily where the processor 102 detects that the acquired motion signals comprises one or more features that are indicative of the subject experiencing swallowing difficulties (e.g. a swallowing impairment). A person skilled in the art will understand that the 'subject swallowing healthily' means that the subject is exhibiting normal swallowing responses or reflexes (e.g. without swallowing impairment and/or difficulty) and that the 'subject swallowing unhealthily' means that the subject is exhibiting abnormal swallowing responses or reflexes (e.g. swallowing with impairment and/or difficulty).

In some embodiments, the processor 102 of the apparatus 100 may be configured to continuously and automatically classify the acquired motion signals as indicative of the subject swallowing healthily or unhealthily. There is thus provided an apparatus for monitoring swallowing in a subject and, in some embodiments, for continuously monitoring swallowing in a subject.

In some embodiments, the processor 102 of the apparatus 100 may be configured to use a classifier (e.g. a trained classifier) to classify the acquired motion signals as indicative of the subject swallowing healthily or unhealthily. For example, a classifier may be trained to discriminate between motion signals that are associated with unhealthy swallowing and motion signals that are associated with healthy swallowing. Thus, a discriminative model for classifying the acquired motion signals into healthy versus unhealthy swallows can be provided according to some embodiments. In some embodiments, a two-class classifier may be used to classify the acquired motion signals as indicative of the subject swallowing healthily or unhealthily. In other embodiments, a three-class classifier may be used to classify the acquired motion signals as indicative of pharyngeal residue, aspiration-penetration, or the subject swallowing healthily. In other embodiments, a four-class classifier may be used to classify the acquired motion signals as indicative of pharyngeal residue, aspiration, penetration, or the subject swallowing healthily.

In some embodiments, the processor 102 of the apparatus 100 may comprise one or more processors 102. The one or more processors 102 can be implemented in numerous ways, with software and/or hardware, to perform the various functions described herein. In some embodiments, each of the one or more processors 102 can be configured to perform individual or multiple steps of the method described herein. In particular implementations, the one or more processors 102 can comprise a plurality of software and/or hardware modules, each configured to perform, or that are for performing, individual or multiple steps of the method described herein.

The one or more processors 102 may comprise one or more microprocessors, one or more multi-core processors and/or one or more digital signal processors (DSPs), one or more processing units, and/or one or more controllers (such as one or more microcontrollers) that may be configured or programmed (e.g. using software or computer program code) to perform the various functions described herein. The one or more processors 102 may be implemented as a combination of dedicated hardware (e.g. amplifiers, pre-amplifiers, analog-to-digital convertors (ADCs) and/or digital-to-analog convertors (DACs)) to perform some functions and one or more processors (e.g. one or more programmed microprocessors, DSPs and associated circuitry) to perform other functions. In some embodiments, the processor 102 of the apparatus 100 may comprise a signal processing module configured to acquire the motion signals from the motion sensor 104 and a classifier module configured to process the acquired motion signals to classify the acquired motion signals as indicative of the subject swallowing healthily or unhealthily.

As illustrated in FIG. 1, in some embodiments, the apparatus 100 may comprise the motion sensor 104 from which the processor 102 is configured to acquire the motion signals that are indicative of swallowing motions transmitted along the feeding tube 204. However, it will be understood that, in other embodiments, the motion sensor 104 may be external to (i.e. separate to or remote from) the apparatus 100. For example, in some embodiments, the motion sensor 104 can be a separate entity or part of another apparatus (e.g. a device). The motion sensor 104 is configured to obtain the motion signals from the feeding tube, when the feeding tube is placed in the esophagus of the subject.

As also illustrated in FIG. 1, in some embodiments, the apparatus 100 may comprise a communications interface (or communications circuitry) 106. Alternatively, or in addition, the communications interface 106 may be external to (e.g. separate to or remote from) the apparatus 100. The communications interface 106 can be for enabling the apparatus 100, or components of the apparatus 100, to communicate with and/or connect to one or more other components, sensors, interfaces, devices, or memories (such as any of those described herein). For example, the communications interface 106 can be for enabling the processor of the apparatus 100 to communicate with and/or connect to the motion sensor 104 described earlier. The communications interface 106 may enable the apparatus 100, or components of the apparatus 100, to communicate and/or connect in any suitable way. For example, the communications interface 106 may enable the apparatus 100, or components of the apparatus 100, to communicate and/or connect wirelessly, via a wired connection, or via any other communication (or data transfer) mechanism. In some wireless embodiments, for example, the communications interface 106 may enable the apparatus 100, or components of the apparatus 100, to use radio frequency (RF), Bluetooth, or any other wireless communication technology to communicate and/or connect.

As illustrated in FIG. 1, in some embodiments, the apparatus 100 may comprise a memory 108. Alternatively, or in addition, the memory 108 may be external to (e.g. separate to or remote from) the apparatus 100. The processor of the apparatus 100 may be configured to communicate with and/or connect to the memory 108. The memory 108 may comprise any type of non-transitory machine-readable medium, such as cache or system memory including volatile and non-volatile computer memory such as random-access memory (RAM), static RAM (SRAM), dynamic RAM (DRAM), read-only memory (ROM), programmable ROM (PROM), erasable PROM (EPROM), and electrically erasable PROM (EEPROM). In some embodiments, the memory 108 can be configured to store program code that can be executed by the processor 102 to cause the apparatus 100 to operate in the manner described herein.

Alternatively, or in addition, in some embodiments, the memory 108 can be configured to store information required by or resulting from the method described herein. For example, in some embodiments, the memory 108 may be configured to store any one or more of the motion signals acquired from a motion sensor 104, the acquired motion signals classified as indicative of the subject swallowing healthily or unhealthily, or any other information, or any combination of information, required by or resulting from the method described herein. In some embodiments, the processor 102 of the apparatus 100 can be configured to control the memory 108 to store information required by or resulting from the method described herein.

As illustrated in FIG. 1, in some embodiments, the apparatus 100 may comprise a user interface 110. Alternatively, or in addition, the user interface 110 may be external to (e.g. separate to or remote from) the apparatus 100. The processor 102 of the apparatus 100 may be configured to communicate with and/or connect to a user interface 110. The user interface 110 can be configured to render (e.g. output, display, or provide) information required by or resulting from the method described herein. For example, in some embodiments, the user interface 110 may be configured to render (e.g. output, display, or provide) one or more of the motion signals acquired from a motion sensor 104, the acquired motion signals classified as indicative of the subject swallowing healthily or unhealthily, or any other information, or any combination of information, required by or resulting from the method described herein. Alternatively, or in addition, the user interface 110 can be configured to receive a user input. For example, the user interface 110 may allow a user to manually enter information or instructions, interact with and/or control the apparatus 100. Thus, the user interface 110 may be any user interface that enables the rendering (or outputting, displaying, or providing) of information and, alternatively or in addition, enables a user to provide a user input. In some embodiments, the processor 102 of the apparatus 100 can be configured to control the user interface 110 to operate in the manner described herein.

For example, the user interface 110 may comprise one or more switches, one or more buttons, a keypad, a keyboard, a mouse, a touch screen or an application (e.g. on a smart device such as a tablet, a smartphone, smartwatch, or any other smart device), a display or display screen, a graphical user interface (GUI) such as a touch screen, or any other visual component, one or more speakers, one or more microphones or any other audio component, one or more lights (e.g. light emitting diode LED lights), a component for providing tactile or haptic feedback (e.g. a vibration function, or any other tactile feedback component), an augmented reality device (e.g. augmented reality glasses, or any other augmented reality device), a smart device (e.g. a smart mirror, a tablet, a smart phone, a smart watch, or any other smart device), or any other user interface, or combination of user interfaces. In some embodiments, the user interface that is controlled to render information may be the same user interface as that which enables the user to provide a user input.

Although not illustrated in FIG. 1, the apparatus 100 may comprise a battery or other power supply for powering the apparatus 100 or means for connecting the apparatus 100 to a mains power supply. It will also be understood that the apparatus 100 may comprise any other component to those described herein or any combination of components.

Thus, there is provided herein an apparatus 100 for monitoring swallowing in a subject, which comprises a processor 102 configured to acquire, from a motion sensor 104, motion signals obtained from a feeding tube (which are indicative of swallowing motions transmitted along the feeding tube), when the feeding tube is placed in the esophagus of the subject, and to process the acquired motion signals to classify the acquired motion signals as indicative of the subject swallowing healthily or unhealthily.

As mentioned earlier, it has been appreciated that feeding tubes are commonly used to feed subjects with swallowing difficulties and this insight has enabled an apparatus 100 to be provided that can non-invasively monitor swallowing in a reliable manner without causing discomfort to the subject beyond that which the subject is already experiencing. The apparatus described herein extends the functionality of feeding tubes for monitoring (e.g. tracking) swallowing in a subject (e.g. swallowing difficulties in a subject according to some embodiments) through movements generated within the esophagus of the subject.

The feeding tube referred to herein can be any type of feeding tube. That is, the feeding tube can be any type of tube suitable for use in feeding (e.g. providing nutrition to) a subject. Examples of a feeding tube include, but are not limited to a nasogastric (NG) feeding tube, an orogastric (OG) feeding tube, or any other type of feeding tube. A nasogastric (NG) feeding tube is a feeding tube that is configured to enter the esophagus of the subject through a nasal cavity of the subject. An orogastric (OG) feeding tube is a feeding tube that is configured to enter the esophagus of the subject through the oral cavity (or the mouth) of the subject.

Figure 2:
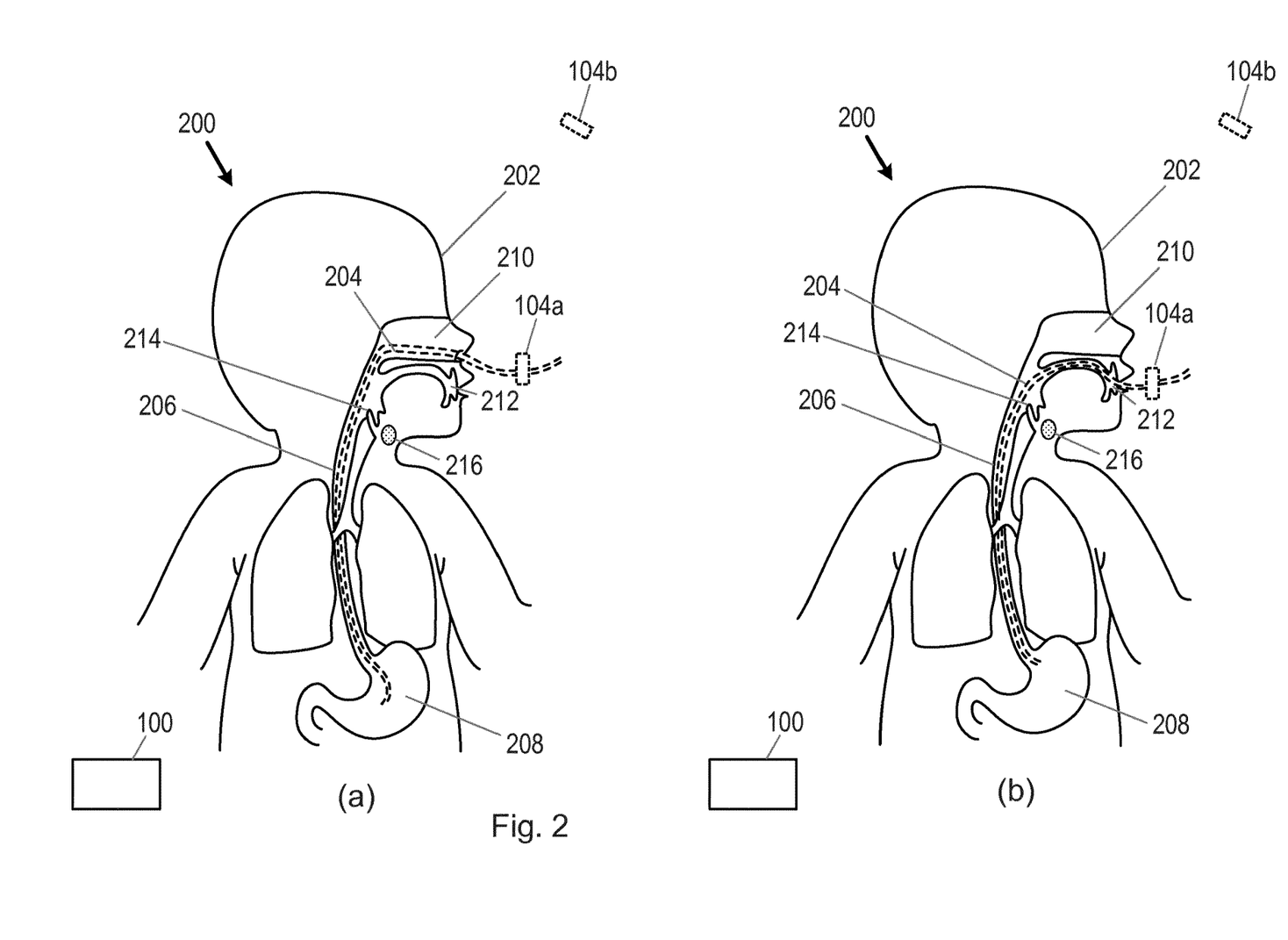
FIG. 2 is a block diagram of a system according to an embodiment.

FIG. 2 illustrates a system 200 comprising the apparatus 100 described earlier for monitoring swallowing in a subject 202 according to an embodiment. More specifically, FIG. 2 illustrates the apparatus 100 in use with a feeding tube 204 placed in the esophagus 206 of the subject 202. Thus, in some embodiments, the system 200 comprising the apparatus 100 can also comprise the feeding tube 204.

Generally, the feeding tube 204 passes through the oropharyngeal cavity of the subject 202 and extends down through the esophagus 206 of the subject 202 to the stomach 208 of the subject 202. FIG. 2(a) illustrates an embodiment where the feeding tube 204 comprises a nasogastric (NG) feeding tube. As illustrated in FIG. 2(a), the nasogastric (NG) feeding tube 204 enters the esophagus 206 of the subject 202 through a nasal cavity 210 of the subject 202. FIG. 2(b) illustrates an embodiment where the feeding tube 204 comprises an orogastric (OG) feeding tube. As illustrated in FIG. 2(b), the orogastric (OG) feeding tube 204 enters the esophagus 206 of the subject 202 through a mouth 212 of the subject 202.

As illustrated in FIG. 2, in some embodiments, the feeding tube 204, when placed in the esophagus 206 of the subject 202, can be positioned in a vicinity of an epiglottis 214 and/or a hyoid bone 216 of the subject 202. The timely movements of the epiglottis 214 and hyoid bone 216 of the subject 202 are critical for healthy swallowing. Thus, monitoring swallowing using a feeding tube 204 positioned in the vicinity of the epiglottis 214 and/or the hyoid bone 216 of the subject 202 can be more reliable.

As illustrated in FIG. 2, in some embodiments, the system 200 can comprise the motion sensor 104, 104a, 104b that is configured to obtain the motion signals from the feeding tube 204, when the feeding tube 204 is placed in the esophagus 206 of the subject 202. As illustrated in FIG. 2, the motion sensor 104, 104a, 104b may be external to (i.e. separate to or remote from) the apparatus 100 according to some embodiments. However, as mentioned earlier, in other embodiments, the apparatus 100 may comprise the motion sensor 104, 104a, 104b. In still other embodiments, the apparatus 100 may comprise one or more motion sensors 104, 104a, 104b and there may also be one or more motion sensors 104, 104a, 104b external to (i.e. separate to or remote from) the apparatus 100.

The motion sensor 104, 104a, 104b referred to herein can be any sensor, or any combination of sensors, suitable for obtaining motion signals from a feeding tube 204 in an esophagus 206 of a subject 202. Examples of a motion sensor 104, 104a, 104b include, but are not limited to, any one or more of an accelerometer 104a (e.g. any one or more of a bi-axial accelerometer, a tri-axial accelerometer, or any other accelerometer, or any combination of accelerometers), a visual sensor 104b (e.g. a camera such as a time of flight (TOF) camera, or any other visual sensor, or any combination of visual sensors), or any other sensor, or any combination of sensors, suitable for obtaining motion signals from a feeding tube 204 in an esophagus 206 of a subject 202.

Thus, in some embodiments, a single motion sensor 104, 104a, 104b or a plurality (e.g. a combination) of motion sensors 104, 104a, 104b may be used to obtain the motion signals from the feeding tube 204, when the feeding tube 204 is placed in the esophagus 206 of the subject 202. For example, one or more accelerometers 104a may be used separately or in combination with one or more visual sensors 104b to obtain the motion signals from the feeding tube 204, when the feeding tube 204 is placed in the esophagus 206 of the subject 202. Similarly, in some embodiments, one or more visual sensors 104b may be used separately or in combination with one or more accelerometers 104a to obtain the motion signals from the feeding tube 204, when the feeding tube 204 is placed in the esophagus 206 of the subject 202. By using a plurality (e.g. a combination) of motion sensors 104, 104a, 104b, the reliability and accuracy of monitoring of swallowing in the subject 202 can be further improved.

In embodiments where the motion sensor 104, 104a, 104b comprises an accelerometer 104a, as illustrated in FIG. 2, the accelerometer 104a may be positioned on (e.g. may sit on or be affixed to) the feeding tube 204. In some embodiments, the accelerometer 104a may be positioned on an external surface of the feeding tube 204. In some embodiments, the accelerometer 104a may be configured to obtain the motion signals from the feeding tube 204, when the feeding tube 204 is placed in the esophagus 206 of the subject 202 by being configured to collect motion samples from the feeding tube 204, when the feeding tube 204 is placed in the esophagus 206 of the subject 202, e.g. at a predefined frequency (such as a frequency that is greater than 5000 Hz).

In embodiments where the motion sensor 104, 104a, 104b comprises a visual sensor 104b, as illustrated in FIG. 2, the visual sensor 104b can be directed at the facial area of the subject 202 and/or the feeding tube 204. The visual sensor 104b may be located (e.g. embedded) in the environment of the subject. In the case of the subject being a premature infant, for example, the visual sensor 104b may be located in the incubator in which the premature infant is present. In embodiments where the motion sensor 104, 104a, 104b comprises a visual sensor 104b, the visual sensor 104b can be configured to obtain the motion signals from the feeding tube 204, when the feeding tube 204 is placed in the esophagus 206 of the subject 202, in the form of images. In these embodiments, the processor 102 of the apparatus 100 can be configured to detect a position of the feeding tube 204 in the images. In embodiments where the visual sensor 104b comprises a time of flight (TOF) camera, an improved three-dimensional reconstruction of the trajectory of the swallowing motions transmitted along the feeding tube 204 is possible.

In some embodiments where the motion sensor 104, 104a, 104b comprises a visual sensor 104b, a part of the feeding tube 204 that is external to the body of the subject 202, when the feeding tube 204 is placed in the esophagus 206 of the subject 202, may comprise a marker. For example, the marker may be provided on the surface of the part of the feeding tube 204 that is external to the body of the subject 202. Examples of a marker include, but are not limited to, one or more stripes on the feeding tube 204, one or more protruding structures on the feeding tube 204 (e.g. a connection added to the feeding tube 204), or any other marker, or any combination of markers. In these embodiments, the processor 102 of the apparatus 100 can be configured to detect the marker in images of the feeding tube 204 acquired from the visual sensor 104b. Thus, in some embodiments, the motion signals obtained from the feeding tube 204 may be acquired by the processor 102 of the apparatus 100 being configured to track the marker in (e.g. consecutive) images of the feeding tube 204 obtained by the visual sensor 104b. In some embodiments, more than one visual sensor 104b may be configured to obtain motion signals from the feeding tube 204. In this way, an improved three-dimensional reconstruction of the trajectory of the swallowing motions transmitted along the feeding tube 204 is possible.

In some embodiments, the motion signals can be obtained from a portion (or segment) of the feeding tube 204 positioned outside (i.e. external to) the body of the subject 202. For example, in embodiments where the feeding tube 204 comprises a nasogastric (NG) feeding tube, such as that illustrated in FIG. 2(a), the motion signals can be obtained from a portion of the feeding tube 204 positioned outside a nasal cavity 210 or, more specifically, outside a nostril, of the subject 202. Similarly, in embodiments where the feeding tube comprises a orogastric (OG) feeding tube, such as that illustrated in FIG. 2(b), the motion signals can be obtained from a portion of the feeding tube 204 positioned outside the mouth 212 of the subject 202. In some embodiments, such as those illustrated in FIG. 2, the motion sensor 104, 104a, 104b may be positioned remote from (or distant to) the body of the subject 202, e.g. either on the feeding tube 204 or elsewhere, such as in the environment of the subject. In this way, the motion sensor 104, 104a, 104b can be provided such that it is not itself in contact with the body of the subject 202.

The motion sensor 104, 104a, 104b can be configured to obtain motion signals from the feeding tube 204, when the feeding tube 204 is placed in the esophagus 206 of the subject 202, in any one or more directions. Thus, the processor 102 of the apparatus 100 can be configured to acquire, from the motion sensor 104, 104a, 104b, motion signals obtained from a feeding tube 204, when placed in the esophagus 206 of the subject 202, in any one or more directions. For example, the motion signals can be acquired in any one or more of a superior-inferior direction, an anterior-posterior direction, and a lateral-medial direction. In some embodiments where the motion sensor 104, 104a, 104b comprises a bi-axial accelerometer 104a, the acquired motion signals can comprise motion signals acquired in any two of these directions. In some embodiments where the motion sensor 104, 104a, 104b comprises a tri-axial accelerometer 104a, the acquired motion signals can comprise motion signals acquired in each of these directions. That is, in some embodiments where the motion sensor 104 comprises a tri-axial accelerometer 104a, the acquired motion signals can comprise motion signals acquired in the superior-inferior direction, the anterior-posterior direction, and the lateral-medial direction.

Figure 3:
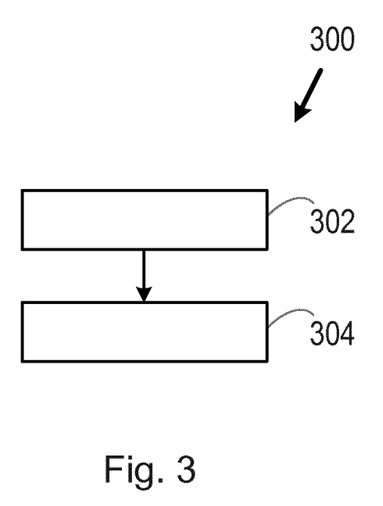
FIG. 3 is flow chart illustrating a method according to an embodiment.

FIG. 3 illustrates a method 300 of operating the apparatus 100 described earlier for monitoring swallowing in a subject 202 according to an embodiment. As described earlier, the apparatus 100 comprises a processor 102. The method 300 illustrated in FIG. 3 can generally be performed by or under the control of the processor 102. With reference to FIG. 3, at block 302 of FIG. 3, motion signals obtained from the feeding tube 204, when the feeding tube 204 is placed in the esophagus 206 of the subject 202, are acquired from the motion sensor 104, 104a, 104b. More specifically, the processor 102 of the apparatus 100 acquires the motion signals obtained from a feeding tube 204, when the feeding tube 204 is placed in the esophagus 206 of the subject 202, from the motion sensor 104, 104a, 104b. As mentioned earlier, the motion signals are indicative of swallowing motions transmitted along the feeding tube 204.

At block 304 of FIG. 3, the acquired motion signals are processed to classify the acquired motion signals as (or detect whether the acquired motion signals are) indicative of the subject 202 swallowing healthily or unhealthily. More specifically, the processor 102 of the apparatus 100 processes the acquired motion signals to classify the acquired motion signals as indicative of the subject 202 swallowing healthily or unhealthily. The processor 102 may process the acquired motion signals to classify the acquired motion signals as indicative of the subject 202 swallowing healthily or unhealthily in the manner described earlier with reference to FIG. 1. For example, in some embodiments, the processor 102 of the apparatus 100 may be configured to process the acquired motion signals to classify the acquired motion signals as indicative of the subject 202 swallowing healthily or unhealthily by being configured to map the acquired motion signals to healthy or unhealthy swallows. Thus, the processor 102 of the apparatus 100 can be configured to map the acquired motion signals into two or more classes according to some embodiments. In some embodiments, the processor 102 of the apparatus 100 can be configured to automatically classify the acquired motion signals as indicative of the subject 202 swallowing healthily or unhealthily. By classifying the acquired motion signals as indicative of the subject 202 swallowing healthily or unhealthily, a tool is provided that can be used to assess a swallowing quality for a subject.

In some embodiments, the processor 102 of the apparatus 100 may be configured to process the acquired motion signals at block 304 of FIG. 3 by being configured to process the acquired motion signals to classify the acquired motion signals as indicative of the subject 202 swallowing healthily or unhealthily according to one or more predefined reference features that are indicative of the subject 202 swallowing healthily or unhealthily. The one or more predefined reference features that are indicative of the subject 202 swallowing healthily or unhealthily may be accessed or acquired by the processor 102 of the apparatus 100, e.g. from a memory 108. In some embodiments, the one or more predefined features can comprise one or more meta-feature representations.

Figure 4:
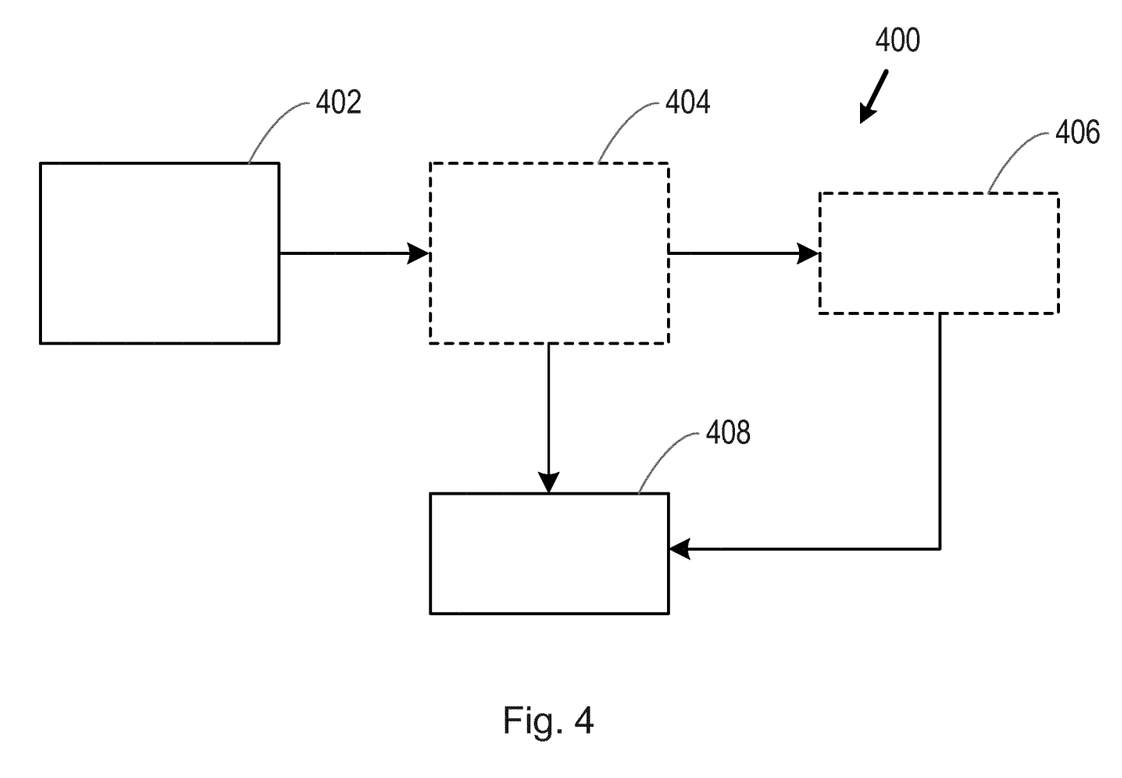
FIG. 4 is flow chart illustrating a method according to another embodiment.

FIG. 4 illustrates a method 400 of operating the apparatus 100 described earlier for monitoring swallowing in a subject 202 according to another embodiment. As described earlier, the apparatus 100 comprises a processor 102. The method 400 illustrated in FIG. 4 can generally be performed by or under the control of the processor 102. With reference to FIG. 4, at block 402 of FIG. 4, motion signals obtained from a feeding tube 204, when the feeding tube 204 is placed in the esophagus 206 of the subject 202, are acquired from the motion sensor 104, 104a, 104b. Thus, at block 402 of FIG.

4, the method described earlier with respect to block 302 of FIG. 3 is performed. More specifically, at block 402 of FIG. 4, the processor 102 of the apparatus 100 acquires the motion signals obtained from a feeding tube 204, when the feeding tube 204 is placed in the esophagus 206 of the subject 202, from the motion sensor 104, 104a, 104b. The motion signals are indicative of swallowing motions transmitted along the feeding tube 204. In some embodiments, the motion signals can be raw motion signals.

Optionally, at block 404 of FIG. 4, the motion signals can be preprocessed and/or conditioned. In some embodiments, for example, at block 404 of FIG. 4, one or more features indicative of swallowing activities may be extracted from the acquired motion signals and the acquired motion signals may be decomposed into a plurality of different segments based on the one or more extracted features. More specifically, the processor 102 of the apparatus 100 may extract the one or more features indicative of swallowing activities from the acquired motion signals and decompose the acquired motion signals into the plurality of different segments based on the one or more extracted features. Thus, according to some embodiments, the processor 102 of the apparatus 100 can be configured to extract one or more features indicative of swallowing activities from the acquired motion signals and decompose the acquired motion signals into a plurality of different segments based on the one or more extracted features.

In some embodiments, the processor 102 of the apparatus 100 may be configured to decompose the acquired motion signals into a plurality of different segments based on the one or more extracted features by identifying one or more segments having a swallowing activity associated therewith based on the one or more extracted features and separating (e.g. isolating) the one or more identified segments from other segments. In this way, for example, noise and other irrelevant sources of variabilities (e.g. body movements of the subject 202) that may be captured by the motion sensor 104, 104a, 104b can be removed from the acquired motion signals. In some embodiments, the processor 102 of the apparatus 100 may be configured to decompose the acquired motion signals into the plurality of different segments based on the one or more extracted features using a wavelet signal decomposition and/or filtering.

Optionally, at block 406 of FIG. 4 according to some embodiments, one or more predefined reference features that are indicative of the subject 202 swallowing healthily or unhealthily may be accessed or acquired by the processor 102 of the apparatus 100 (e.g. from a memory 108). Thus, according to some embodiments, the processor 102 of the apparatus 100 can be configured to access or acquire (e.g. from a memory 108) one or more predefined reference features indicative of the subject 202 swallowing healthily or unhealthily. The one or more predefined features can, for example, comprise one or more meta-feature representations according to some embodiments.

At block 408 of FIG. 4, the acquired motion signals are processed to classify the acquired motion signals as indicative of the subject 202 swallowing healthily or unhealthily. Thus, at block 408 of FIG. 4, the method described earlier with respect to block 304 of FIG. 3 is performed. More specifically, the processor 102 of the apparatus 100 processes the acquired motion signals to classify the acquired motion signals as indicative of the subject 202 swallowing healthily or unhealthily. In the embodiment illustrated in FIG. 4, the processor 102 of the apparatus 100 processes the acquired motion signals (at block 404 of FIG. 4) by processing the plurality of different segments to classify the acquired motion signals as indicative of the subject 202 swallowing healthily or unhealthily. Thus, according to some embodiments, the processor 102 of the apparatus 100 can be configured to process the acquired motion signals (at block 408 of FIG. 4) by being configured to process the plurality of different segments to classify the acquired motion signals as indicative of the subject 202 swallowing healthily or unhealthily.

In embodiments where one or more predefined reference features indicative of the subject 202 swallowing healthily or unhealthily are accessed or acquired at block 406 of FIG. 4, the processor 102 of the apparatus 100 may be configured to process the acquired motion signals at block 408 of FIG. 4 by being configured to process the plurality of different segments to classify the acquired motion signals as indicative of the subject 202 swallowing healthily or unhealthily according to one or more predefined reference features that are indicative of the subject 202 swallowing healthily or unhealthily.

In any of the embodiments described herein, such as either of those illustrated in FIG. 3 or 4, the processor 102 of the apparatus 100 may be configured to process the acquired motion signals (e.g. at block 304 of FIG. 3 or at block 408 of FIG. 4) using a classifier algorithm. In some embodiments, for example, the classifier algorithm may be present in the processor 102 of the apparatus 100. The classifier algorithm can be developed, for example, by acquiring (e.g. concurrent) images obtained from an existing technique for monitoring swallowing to obtain a direct observation (or ground truth) of swallowing in a subject and also by acquiring motion signals indicative of swallowing in the subject from a motion sensor 104 (e.g. an accelerometer 104a and/or visual sensor 104b) in the manner described earlier. The existing technique for monitoring swallowing may, for example, comprise a videofluoroscopy swallowing study (VFSS).

The acquired motion signals may be annotated based on the acquired images, e.g. by a medical professional (such as a speech-language pathologist) to indicate whether those acquired motion signals are indicative of healthily or unhealthily swallowing. In some embodiments, the acquired images may be rated on a scale from healthily swallowing to unhealthy swallowing based on the acquired images, such as by using the Penetration-Aspiration scale. The annotated motion signals can be used to develop and verify the efficacy of the classification algorithm used by the processor 102 of the apparatus 100 to classify the motion signals acquired in the manner described herein.

In any of the embodiments described herein, such as either of those illustrated in FIG. 3 or 4, the classifier algorithm used by the processor 102 of the apparatus 100 to process the acquired motion signals (e.g. at block 304 of FIG. 3 or at block 408 of FIG. 4) may comprise a gated recurrent deep neural network (RNN). Thus, according to some embodiments, the processor 102 of the apparatus 100 may be configured to process the acquired motion signals (e.g. at block 304 of FIG. 3 or at block 408 of FIG. 4) using a gated recurrent deep neural network (RNN) to classify the acquired motion signals as indicative of the subject 202 swallowing healthily or unhealthily. In some embodiments, a gated recurrent deep neural network (RNN) may be configured to decompose the acquired motion signals into different levels of abstractions salient to discriminating between different swallowing classes. In some embodiments, the classification may be augmented with time-frequency meta-features reported as salient in swallowing characterization.

Although not illustrated in the figures, in any of the embodiments described herein, such as either of those illustrated in FIG. 3 or 4, the processor 102 of the apparatus 100 may be further configured to determine whether the subject 202 is ready for independent oral feeding based on whether the acquired motion signals are classified as indicative of the subject 202 swallowing healthily or unhealthily. For example, the processor 102 of the apparatus 100 may be configured to determine that the subject 202 is ready for independent oral feeding where the acquired motion signals are classified as indicative of the subject 202 swallowing healthily. On the other hand, for example, the processor 102 of the apparatus 100 may be configured to determine that the subject 202 is not ready for independent oral feeding where the acquired motion signals are classified as indicative of the subject 202 swallowing unhealthily.

Thus, in some embodiments, the apparatus 100, system 200, and method 300, 400 described herein can aid in identifying the readiness of a subject for independent oral feeding, which can help to avoid (or at least reduce) clinical misjudgments as to whether to start (or restart) independent oral feeding. In this way, the necessary calories required by the subject can be preserved since oral aversions (due to negative feeding encounters when the subject is not actually ready for independent oral feeding) are decreased and an improved quality of care can be provided for the subject. Moreover, in addition to aiding clinicians in deciding the timing and progression of independent oral feeding of the subject 202, the apparatus 100, system 200, and method 300, 400 described herein can also aid clinicians in deciding a timing for discharging the subject 202 from an intensive care unit or medical facility (e.g. a hospital).

In addition to the apparatus 100, system 200 and method 300, 400 described earlier, there is also provided a computer program product comprising a computer readable medium. The computer readable medium has a computer readable code embodied therein. The computer readable code is configured such that, on execution by a suitable computer or processor, the computer or processor is caused to perform the method described herein. The computer readable medium may be, for example, any entity or device capable of carrying the computer program product. For example, the computer readable medium may include a data storage, such as a ROM (such as a CD-ROM or a semiconductor ROM) or a magnetic recording medium (such as a hard disk). Furthermore, the computer readable medium may be a transmissible carrier, such as an electric or optical signal, which may be conveyed via electric or optical cable or by radio or other means. When the computer program product is embodied in such a signal, the computer readable medium may be constituted by such a cable or other device or means. Alternatively, the computer readable medium may be an integrated circuit in which the computer program product is embedded, the integrated circuit being adapted to perform, or used in the performance of, the method described herein.

There is thus provided herein an improved apparatus 100, system 200, method 300, 400 and computer program product for monitoring swallowing in a subject 202. In some embodiments, the apparatus 100, system 200 method 300, 400 and/or computer program product described herein may be for tracking swallowing difficulties in a subject 202.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for monitoring swallowing in a subject, comprising:
   a feeding tube structured and configured to be placed in the esophagus of the subject;
   a motion sensor structured and configured to acquire motion signals from the feeding tube when the feeding tube is placed in the esophagus of the subject, wherein the motion signals are indicative of swallowing motions of the subject transmitted along the feeding tube; and
   a processor configured to:
      acquire the motion signals from the motion sensor;
      extract one or more features indicative of swallowing activities from the acquired motion signals;
      decompose the acquired motion signals into a plurality of different segments based on the one or more extracted features; and
      process the plurality of different segments to classify the acquired motion signals as indicative of the subject swallowing healthily or unhealthily.

2. The apparatus as claimed in claim 1, wherein the motion signals are obtained from a portion of the feeding tube positioned outside the body of the subject.

3. The apparatus as claimed in claim 1, wherein the motion sensor is positioned remote from the body of the subject.

4. The apparatus as claimed in claim 1, wherein the motion sensor comprises an accelerometer positioned on the feeding tube.

5. The apparatus as claimed in claim 4, wherein the accelerometer comprises any-one or more of a bi-axial accelerometer-and-or a tri-axial accelerometer.

6. The apparatus as claimed in claim 5, wherein the accelerometer comprises the tri-axial accelerometer and the acquired motion signals comprise motion signals acquired in a superior-inferior direction, an anterior-posterior direction, and a lateral-medial direction.

7. The apparatus as claimed in claim 1, wherein the motion sensor comprises a visual sensor directed at the feeding tube.

8. The apparatus as claimed in claim 1, wherein the feeding tube when placed in the esophagus of the subject is positioned in a vicinity of at least one of an epiglottis or a hyoid bone of the subject.

9. The apparatus as claimed in claim 1, wherein the processor is further configured to:
   determine whether the subject is ready for independent oral feeding based on whether the acquired motion signals are classified as indicative of the subject swallowing healthily or unhealthily.

10. An apparatus for monitoring swallowing in a subject, the apparatus comprising:
   a feeding tube structured and configured to be placed in the esophagus of the subject;

a motion sensor structured and configured to acquire motion signals from the feeding tube when the feeding tube is placed in the esophagus of the subject, wherein the motion signals are indicative of swallowing motions of the subject transmitted along the feeding tube; and a processor configured to:

acquire the motion signals from the motion sensor and process the acquired motion signals using a gated recurrent deep neural network to classify the acquired motion signals as indicative of the subject swallowing healthily or unhealthily.

11. A method for monitoring swallowing in a subject, the method comprising:

placing a feeding tube in the esophagus of the subject;

acquiring with a motion sensor motion signals from the feeding tube when the feeding tube is placed in the esophagus of the subject, wherein the motion signals are indicative of swallowing motions of the subject transmitted along the feeding tube;

acquiring the motion signals from the motion sensor in a processor;

extracting in the processor one or more features indicative of swallowing activities from the acquired motion signals;

decomposing in the processor the acquired motion signals into a plurality of different segments based on the one or more extracted features; and processing in the processor the plurality of different segments to classify the acquired motion signals as indicative of the subject swallowing healthily or unhealthily.

\* \* \* \* \*